United States Patent [19]
Jampani et al.

[11] Patent Number: 5,997,893
[45] Date of Patent: Dec. 7, 1999

[54] ALCOHOL BASED ANTI-MICROBIAL COMPOSITIONS WITH COSMETIC APPEARANCE

[75] Inventors: Hanuman B. Jampani, Grapevine; Jerry L. Newman, Arlington; Anthony W. Newman, Fortworth, all of Tex.

[73] Assignee: Ethicon, Inc., Somerville, N.J.

[21] Appl. No.: 09/009,491

[22] Filed: Jan. 20, 1998

[51] Int. Cl.⁶ .......................... A01N 25/00; A01N 33/12; A01N 31/00; A61K 7/00
[52] U.S. Cl. .......................... 424/405; 424/401; 514/358; 514/642; 514/724; 514/758; 514/937; 514/944
[58] Field of Search .................................. 424/401, 405; 514/642, 358, 724, 758, 937, 944

[56] References Cited

U.S. PATENT DOCUMENTS

| | | |
|---|---|---|
| 2,798,053 | 7/1957 | Brown . |
| 3,133,865 | 5/1964 | Richardson et al. . |
| 3,886,277 | 5/1975 | Randebrook et al. . |
| 4,134,412 | 1/1979 | Gross et al. . |
| 4,202,881 | 5/1980 | Gross et al. . |
| 4,257,907 | 3/1981 | Langguth et al. . |
| 4,268,424 | 5/1981 | Hall et al. . |
| 4,303,543 | 12/1981 | Mansy . |
| 4,326,997 | 4/1982 | Willis et al. . |
| 4,423,041 | 12/1983 | Clum et al. ............................. 424/184 |
| 4,426,310 | 1/1984 | Verunica . |
| 4,464,293 | 8/1984 | Dobrin . |
| 4,474,807 | 10/1984 | Gerhardt et al. . |
| 4,690,821 | 9/1987 | Smith et al. . |
| 4,804,750 | 2/1989 | Nishimura et al. . |
| 4,816,451 | 3/1989 | Schriewer et al. . |
| 4,849,455 | 7/1989 | Eggers et al. . |
| 4,923,862 | 5/1990 | Hirota . |
| 4,956,170 | 9/1990 | Lee ....................................... 514/772.1 |
| 4,966,754 | 10/1990 | Purohit et al. . |
| 5,004,598 | 4/1991 | Lochead et al. . |
| 5,053,407 | 10/1991 | Hayakawa et al. . |
| 5,098,717 | 3/1992 | Blackman . |
| 5,109,019 | 4/1992 | Lehmann et al. . |
| 5,164,107 | 11/1992 | Khan et al. . |
| 5,180,061 | 1/1993 | Khan et al. . |
| 5,180,749 | 1/1993 | Cusak et al. . |
| 5,188,756 | 2/1993 | Baker et al. ........................ 252/174.15 |
| 5,288,486 | 2/1994 | White . |
| 5,308,890 | 5/1994 | Snyder . |
| 5,326,492 | 7/1994 | Hodam, Jr. . |
| 5,335,373 | 8/1994 | Dangman et al. . |
| 5,336,305 | 8/1994 | Staats . |
| 5,401,741 | 3/1995 | Saro et al. . |
| 5,403,587 | 4/1995 | McCue et al. . |
| 5,403,864 | 4/1995 | Bruch et al. . |
| 5,416,109 | 5/1995 | Donofrio et al. . |
| 5,420,104 | 5/1995 | Holzner et al. . |
| 5,512,199 | 4/1996 | Khan et al. . |
| 5,540,853 | 7/1996 | Trinh et al. . |
| 5,567,428 | 10/1996 | Hughes ..................................... 424/401 |
| 5,607,681 | 3/1997 | Galley et al. . |
| 5,622,694 | 4/1997 | Torgerson et al. ................. 424/70.122 |
| 5,626,837 | 5/1997 | Shimada et al. . |
| 5,661,170 | 8/1997 | Chodosh . |
| 5,665,742 | 9/1997 | Mori et al. . |
| 5,725,845 | 3/1998 | Krog et al. ................................. 424/64 |
| 5,750,579 | 5/1998 | Kamishita et al. ................... 514/772.6 |
| 5,759,969 | 6/1998 | Tsaur et al. .............................. 510/158 |
| 5,957,908 | 9/1990 | Nelson . |

FOREIGN PATENT DOCUMENTS

| | | |
|---|---|---|
| 600269 | 5/1987 | Australia . |
| WO 94/27436 | 12/1994 | WIPO . |

OTHER PUBLICATIONS

Lee W. Bush, Leslee M. Benson, and John H. White, Pig Skin Test Subtrate for Evaluating Topical Antimicrobial Activity, Sep. 1986, Journal of Clinical Microbiology.

*Primary Examiner*—Shelley A. Dodson
*Assistant Examiner*—Marina Lamm
*Attorney, Agent, or Firm*—Joseph F. Leightner

[57] ABSTRACT

The present invention provides antimicrobial compositions containing high levels of alcohol, carbomer polymers and antimicrobial agents. The present invention provides stable, high viscosity antimicrobial formulations possessing cosmetic characteristics.

16 Claims, No Drawings

ALCOHOL BASED ANTI-MICROBIAL COMPOSITIONS WITH COSMETIC APPEARANCE

This application is related to my U.S. patent applications Ser. Nos. 09/009,596, entitled ANTI-MICROBIAL COMPOSITION; and 09/009,489, entitled LOW TACK LOTION, GELS AND CREAMS, all concurrently filed herewith and which are assigned to assignee of the present invention and incorporated by reference as if fully set forth herein.

The present invention relates to anti-microbial compositions, more particularly to alcohol-containing cationic antimicrobial compounds that are compatible with emollients and cationic compounds thereby providing lotion-like appearance and properties.

BACKGROUND OF THE INVENTION

Alcohols and alcohol-containing mixtures are known to possess bactericidal activity and to prevent nosocomial infections in hospital settings between patients, nurses and doctors. The use of alcohol based compositions is declining due to their inherent dehydrating properties which is caused by the denaturing and delipidizing of the skin's lipid molecules. It is appreciated in the art that lipids in stratum corneum of the skin are important in the barrier properties.

In an attempt to address the dehydration and delipidization problem, attempts have been made to minimize the dehydration effects of the alcohol systems. U.S. Pat. No. 5,288,486 discloses the use of polymeric viscosifying agents which have been added to the compositions to reduce evaporation and provide moisturization. While this approach has reduced the evaporation rate of the alcohol, the compositions lack the feel, moisturization and non-greasy texture sought by medical professionals.

It would be highly desirable to provide an effective alcohol-containing antimicrobial composition that possesses the feel and moisturizing attributes of a hand cream and lotion. It is also desirable to use chemical ingredients that provide the appearance of moisturizing products to overcome the perceived drying of topical alcohol-containing formulations. These two aspects in any product or a formulation would provide multi-functions, such as antibacterial efficacy, mildness, moisturization and protection.

SUMMARY OF THE INVENTION

The present invention provides a highly effective antimicrobial composition that also possesses moisturizing attributes and does not become greasy to the touch. In particular, one aspect of the invention provides an aqueous antimicrobial composition comprising alcohol, an effective amount of a antimicrobial compound, particularly cationic compounds, and a carbomer polymer, the composition having a viscosity of greater than 5,000 centipoise.

In a second embodiment of the invention the antimicrobial composition additionally is provided with an effective amount of phenylethyl dimethicone, stearoxy-trimethylsilane and stearyl alcohol to provide an opaque, milky white lotion.

In a third embodiment of the invention the antimicrobial formulation additionally contains an effective amount of cetyl lactate and ($C_{12}$–$C_{15}$) alkyl lactates and/or an effective amount of cyclomethicone. The addition of these ingredients allows the formulation to incorporate more essential oils and volatile compounds which improves the overall performance of the composition.

Another embodiment of the present invention provides a method for disinfecting surfaces by contacting the surface with an effective amount of the antimicrobial composition.

DETAILED DESCRIPTION OF THE INVENTION

The present invention relates to antimicrobial alcohol-containing compositions containing a carbomer polymer, a cationic antimicrobial compound and a preferably a silicone wax. A complexing agent may additionally be provided. The balance of the composition is water, typically from about 15 to about 40 percent by weight.

The alcohols useful in the present invention include n-propyl and iso-propyl alcohol and ethyl alcohol. The alcohols are typically employed at a level of from about 40 to about 80 percent by volume, preferably from about 60 to about 75 percent by volume. Ethyl alcohol is typically used in the present invention from about 20 to about 55 weight percent, preferably from about 30 to about 50 and most preferably from about 35 to about 48 weight percent. When a mixture of alcohols are employed ethyl alcohol is typically used from 20–55 weight percent, iso-propyl alcohol from about 5 to about 30 weight percent and n-propyl alcohol from about 2 to about 40 weight percent. More preferably the amount of ethyl alcohol is from about 30 to about 50 weight percent, iso-propyl alcohol from about 8 to about 20 weight percent and n-propyl alcohol from about 4 to about 20 weight percent.

The antimicrobial cationic compositions suitable for use in the present invention include cationic compounds which are well know in the art. Suitable compounds include benzethonium chloride, benzalkonium chloride, cetyl pyridinium chloride, bisdequalinium chloride, cetylalkonium chloride, methyl benzethonium chloride, phenoctide, tibezonium iodide, triclobisonium chloride, laurolinium acetate, mixtures thereof and the like. The present invention overcomes the destability problem encountered when cationic compounds are mixed with carbomer polymers. The total cationic compound level is typically from about 0.05 to about 0.5, preferably from about 0.08 to about 0.3 percent by weight, and most preferably from about 0.09 to about 0.2 weight percent.

The present invention also employs thickening agents of acrylic acid which are crosslinked with an unsaturated polyfunctional agent such as polyallyl ether of sucrose. These acrylic acid functionalized polymers, commonly known as carbomers, are disclosed in U.S. Pat. Nos. 2,798,053 and 3,133,865 herein incorporated by reference.

The selection of the proper carbomer provides the antimicrobial formulation with the desired viscosity values. In order to have the desired feel the viscosity of the formulation must have a value of greater than about 5,000 centipoise. More preferably the formulations will have a viscosity of from about 9,000 to about 22,000 and most preferably from about 11,000 to about 20,000 centipoise as measured at 25° C.

A thickening agent, which is an addition agent comprised of an acrylic acid polymer crosslinked with an unsaturated polyallyl ether of sucrose is employed. The polymers are used in an amount sufficient to obtain a gelled composition of viscosity in the desired range.

A number of these polymers, known in the art as carbomers are commercially marketed by B. F. Goodrich, (Cleveland, Ohio) such as CARBOPOL® 934, 940 and 941; and by R.I.T.A. (Crystal Lake, Ill.)as ACRITAMER® 934, 940 and 941, respectively. Typically the carbomer compounds are used from about 0.2 to about 2.0 percent by weight, and are preferably employed at a level of from about 0.4 to about 0.7 by weight of the total antimicrobial composition.

A preferred carbomer polymer, among several preferred carbomers, is R.I.T.A. ACRITAMER® 505E, a polyvinyl carboxy polymer crosslinked with ethers of pentaerythritol. ACRITAMER® 505E is preferred as a gelling agent or viscosity enhancer because it provides a transparent or translucent gel in the present invention.

The most preferred carbomer is ULTREZ® 10 (available from B. F. Goodrich)an oil in water emulsion of a modified acrylic copolymer comprising of a major portion of a monoolefinically unsaturated carboxylic acid monomer or its anhydride having a length of from about 3 to 6 carbon atoms and a minor portion of a $C_8$–$C_{30}$ chain acrylate or methacrylate ester monomer wherein the carboxylic acid or its anhydride is from about 80 to about 99% by weight and the a $C_8$–$C_{30}$ chain acrylate or methacrylate ester monomer is from about 1% to about 20% by weight. The polymer is described in U.S. Pat. No. 5,004,598, hereby incorporated by reference in its entirety.

The present invention provides surprising and unexpected results in that contrary to the disclosure provided in its literature, ULTREZ® 10 provides excellent viscosity in the presence of ions. This is surprising in that ULTREZ® 10 product literature discloses that the product is not stable, and should be used in combination with other polymers which have good performance in the presence of ions.

Optionally other thickening agents may also be employed so long as the resulting composition does not leave a residue on the skin that is overly sticky and has acceptable tactile characteristics. Suitable agents are known in the art and include gums, substituted gums such as propylene glycol ether of guar gums, xanthan gum and the like.

In addition to the above identified materials in the formulation it is highly desirable to include other ingredients in order to enhance the performance or feeling of the composition. These ingredients include carrier materials such as phenylethyl dimethicone (commercially available as SILSOFT® PEDM), dimethicone, and cyclomethicone. Phenylethyl dimethicone is employed of from about 0.1 to about 2.0 percent by weight, preferably from 0.1 to about 1.0 and most preferably from 0.25 to about 0.5 weight percent. Cyclomethicone is typically used from about 0.6 to about 5.0, preferably from about 0.75 to about 2.0 and most preferably from about 0.8 to about 1.5 weight percent. The addition of the carrier component improves the stability of the dispersion of the formulation and allows a stable lotion formulation. For example, the elimination of the carrier agent will allow the silicone wax (stearoxy-trimethyl silane) to be deposited on the hands of the user.

Other useful ingredients include lubricants such as phenylethyl dimethicone, a polymeric silicone, which is advantageously employed to disperse other ingredients. In absence of this compound, waxes such as Dow Corning Wax® 580, (a mixture of stearyloxytrimethylsilane and stearyl alcohol) was found to be incompatible with other ingredients. When such formulations are applied on to hands, "flaking" was observed. Flaking is generally believed to occur due to the crystallization of the wax upon the quick evaporation of low volatile components, i.e. the alcohol and cyclomethicone.

Optionally, the present invention also employs complexing agents at a level of from 0.05 to about 0.5 percent by weight. Suitable complexing agents include ethylenediaminetetra-acetic acid (EDTA) and various salts of EDTA, including sodium, disodium, potassium, calcium and the like.

In order to provide skin compatible and non-irritating formulation pH adjusters are employed to gel the carbomer and provide a pH that is neutral to slightly acid (pH about 5.7-about 7.0). Other ingredients include essential oils such as lemon grass oil, Australian tree tea oil, thyme oil, lavender oil, clove oil and the like. The essential oils are used at a level of from about 0.1 to about 5.0%. The essential oils increase the emolliency, penetration and moisturization properties of the present invention.

In the present invention, the stability to the addition of other ingredients such as essential oils, waxes, high boiling solvents such as iso-propyl alcohol (82.5° C.), n-propyl alcohol (97.2° C.) is relatively low. The instability manifests itself in the reduction of the viscosity of the formulation and is also called "load" on to the carbomer. Due to this load, particularly at high alcohol concentrations a phenomenon known as "balling" is observed upon application to the hands. Balling is the process of forming small balls believed to be consisting of carbomer and other ingredients of the formulations. Similar observations are not made when the high alcohol content product is applied after rinsing the hands with water followed by toweling. It is believed that balling occurs when there is a limited amount of water present in the formulation. In these limited water circumstances it is believed that the carbomer becomes hydrated with skin moisture while ionic molecules acting on carbomer and skin electrolytes, the load on the carbomer becomes too great which results in the balling of the carbomer and other ingredients in the hand.

Due to the high alcohol levels found in the formulations, the present invention is effective as a dirt indicators and dirt remover. However, unlike other alcohol-based formulations the present invention is also capable of providing moisturize to the hands due to the incorporation of high levels of emollients and natural oils. Formulations containing higher amounts of water (20–40% by volume) and lower percentage of alcohols (50–60% by volume) didn't exhibit such a phenomenon but observed an improvement in the lotion appearance, i.e. opaque, milky white appearance.

In another embodiment of the invention, the incorporation of a wax enhances the lotion appearance to a buttery look of base formula with ULTREZ® 10. For example, stearoxy trimethyl stearate is typically used from about 0.01 to about 1.0, preferably from 0.02 to about 0.5 and most preferably from 0.025 to about 0.1 weight percent. Cetyl lactate is used from about 0.3 to about 1.5, preferably from about 0.4 to about 1.0 and most preferably from 0.4 to about 0.8 weight percent. $C_{12}$–$C_{15}$ alkyl lactates are used from about 0.2 to about 2.0,preferably from 0.4 to about 1.5 and most preferably from about 0.5 to about 1.25 weight percent. Experimental formulations have revealed preferred components and their proportions to obtain stable formulations without flaking and/or balling.

| | |
|---|---|
| Wax preferably (Dow Corning ® Wax 580) | 0.01–1.00 |
| Cyclomethicone (decamethylcycol-pentasiloxane) | 0.75–5.0 |
| SILSOFT ® PEDM | 0.1–2.0 |
| Dimethicone (optional) | 0.2–2.0 |
| $C_{12}$–$C_{15}$ alkyl lactate | 0.2–2.0 |
| Cetyl lactate | 0.2–2.0 |
| Carbomer (such as ULTREZ 10) | 0.2–2.0 |

The amount of highly volatile substances such as alcohols, like ethyl alcohol and other components such as ULTREZ 10, Dow Corning® 580 Wax, cyclomethicone, phenylethyl dimethicone and essential oils, are dependent on the load. The level of these components is an important factor to obtain stable and formulations having the desired viscosity. The preferred ratio of the components of the invention are silicone wax, such as stearoxytrimethylsilane 0.1%/ phenylethyl dimethicone 1.0%/carbomer 2.3%/ cyclomethicone 5.6% with the remainder of the composition containing primarily alcohol and water, with other ingredients provided at lower levels.

Listed below are typical ranges for components of the present invention.

| Ingredients | Percentage by weight |
|---|---|
| Deionized water | 20–40 |
| Alcohol (percent by volume) | 60–70 |
| Cationic antimicrobial compounds, such as benzethonium chloride, benzalkonium chloride and cetyl pyridinium chloride | 0.05–0.5 |
| Complexing agent, such as Na$_2$EDTA | 0.01–0.1 |
| Carbomer Polymer such as ULTREZ ® 10 | 0.2–2.0 |
| Wax such as (Dow Corning ® Wax 580) | 0.01–1.00 |
| Cyclomethicone | 0.75–5.0 |
| Load enhancers, such as phenylethyl dimethicone and dimethicone | 0.1–2.0 |
| Detackifiers such as C$_{12}$–C$_{15}$ alkyl lactate | 0.2–2.0 |
| cetyl lactate | 0.3–1.5 |

The compositions of the present invention may also contain other ingredients such as emollients, used from about 1 to about 20; preferably from 10–15 percent by weight of the total formulation weight, moisturizers, used from about 1 to about 40; preferably from 10–20 percent by weight of the total formulation weight, fragrances, colors and the like which are known in the art.

These compositions are not limited to the cleansing of surfaces but may also be extended to scrubs, hand disinfectants, incontinence, home health care, wound healing and wound care products and consumer products. In particular the present invention is useful in disinfecting hands, infected sites, presurgical cutaneous sites, acne sites and injection sites, such where vaccines, shots, and catheters are to be provided. An effective amount of the composition is applied to the area which is to be disinfected. Typically, from about 0.5 to about 10 milliliters, preferably from about 1.0 to about 8, and most preferably from about 2.5 to about 5 milliliters of the antimicrobial composition is applied. This amount of the antimicrobial composition is found to be effective, to provide a log$_{10}$ reduction of 2 or more in the microbe population.

In addition the present invention is well suited for disinfecting hard surfaces such as tables, countertops, operation room equipment and the like. The formulations of the present invention are non-irritating and not skin sensitizers. Surprisingly and unexpectedly the compositions of the present invention were also found to be moisturizing. This is surprising in that the compositions contain high levels, more than 50% by weight, of alcohol which are known to be drying to the skin.

The following commercially available materials were used in the following examples:

AD MOD I is a fragrance available from International Flavor and Fragrance.

AMP-95 is a mixture of 2-amino-2-methyl-1-propanol, 2-(methylamino)-2-methyl-1-propanol and water in a ratio of about 90:5:5, commercially available from Angus Chemical Company.

CERAPHYL® 28 is primarily cetyl lactate, a waxy solid commercially available from ISP Van Dyk Inc.

CERAPHYL® 41 is a mixture of $C_{12}$–$C_5$ alkyl lactates, commercially available from ISP Van Dyk Inc.

COSMOCIL® is 20% polyhexamethylene biguinide hydrochloride solution, available from Zeneca Biocides.

DOW CORNING® 245 fluid is cylomethicone.

DOW CORNING® 580 wax a mixture of wax stearoxytrimethyl silane and stearyl alcohol.

ESS 9090 IC is a fragrance available from Givudan-Roure Corporation.

GERMABEN II is a mixture of diazolidinyl urea (about 30%), methylparaben (about 11%) and propyl paraben (about 3%) and propylene glycol (about 56%) available from Sutton Laboratories.

GERMALL PLUS is a mixture of 3-Iodo-2-propynlbutylcarbamate (about 1%) and diazolidinyl urea (about 99%) available from Sutton Laboratories.

PHOSPHOLIPID CDM is cocophosphatidyl (PG)-diamonium chloirde, a co-synthetic, biomimetic, phospholipid available from Mona Industries, Inc.

SILSOFT® PEDM- phenylethyl dimethicone, available from Witco Corporation, OSi Specialties, Inc.

The following examples are illustrative of the present invention and are not to be limited thereto. As used herein cps is understood to be centipoise and unless otherwise directed all percentages are by weight. All recordings were done at 25° C.

EXAMPLE 1

The following formulation was prepared and the weight percent of the component used were as follows. The alcohol levels are reported by volume and the pH of the mixtures were adjusted to be approximately 6.4.

Formulation 1 ethanol 70%; ACRITAMER 505E 0.45; glycerin 3; cyclomethicone (245) 1; dimethicone (225) 0.5; Dow Corning® 580 Wax 0.25; SILSOFT® PEDM 1; LEX-OREZ® 100 0.25; CERAPHYL-41 0.5; CERAPHYL®-28; triclosan 0.3; ESS 9090IC 0.06; and deionized water. The formulation was found to have a Brookfield viscosity of 14,000 centipoise as measured with a #4 spindle at 10 RPM.

Formulation 2—Formulation 1 was made again except that 0.2 of benzethonium chloride was added. The viscosity of the resulting formulation dropped to 540 cps.

Formulation 3—Formulation 1 was made except that the triethanolamine was removed and Na$_2$EDTA was added at a level of 0.18%. The viscosity of the formulation was 4320 cps.

Formulation 4—Formulation 1 was repeated except that instead of using 70% ethyl alcohol, the alcohol content was replaced with 40% ethyl alcohol, 25% iso-propyl alcohol and 5% n-propyl alcohol. The viscosity of the formulation was 6,780 cps.

TABLE 1

Formulation viscosities with cationics and salts

| Formulation | Viscosity (cps) | Viscosity Reduction (%) |
|---|---|---|
| 1 (Base formula with ACRITAMER ® 505E) | 14,000 | — |
| 2 (Base formula with ACRITAMER ® 505E plus benzethonium chloride) | 540 | 96.1 |
| 3 (Base formula with ACRITAMER ® 505E plus disodium ETDA) | 4,320 | 69.1 |
| 4 (Base formula with ACRITAMER ® 505E plus ethyl alcohol, iso-propyl alcohol and n-propyl alcohol) | 6,780 | 51.6 |

R.I.T.A. ACRITAMER® 505E, a polyvinyl carboxy polymer comprised of crosslinked with ethers of pentaerythritol was found to be unstable between 0.45 and 0.6% by weight in presence of complexing agents such as disodium EDTA and cationic molecules like benzalkonium chloride (alkyl dimethyl benzyl ammonium chloride) and benzethonium chloride (diisobutyl phenoxy ethoxy ethyl dimethyl benzyl ammonium chloride) at different concentration levels.

Addition of benzethonium chloride at 0.2 weight, disodium EDTA 0.018, and a mixture of ethyl alcohol, iso-propyl alcohol n-propyl alcohol (45:25:5) resulted in viscosity reductions 96.1%, 69.1% and 51.6%, respectively. (Table 1).

EXAMPLE 2

Formulation 5 was prepared containing the following ingredients: ethyl alcohol 70; ULTREZ® 10 0.60; glycerin 1.5; cyclomethicone 1.5; dimethicone 0.5; Dow Corning® 580 wax 0.25; SILSOFT PEDM 1.0; LEXOREZ® 100 0.25; CERAPHYL-41 0.5; CERAPHYL-28 0.5; triclosan 0.3; AMP-95 (pH adjuster); ESS 9090 IC 0.06 and deionized water. The viscosity of the solution was 21,600.

Formulation 6 Formulation 5 was prepared and 0.2% of benzethonium chloride was added. The viscosity of the resulting solution decreased to 7,200.

Formulation 7 Formulation 5 was prepared except that $Na_2EDTA$ was added to the formulation. The viscosity was 12,540.

Formulation 8 Formulation 5 was prepared except that the AMP-95 was eliminated and in its place triethanolamine was added to the formulation. The viscosity was 20,820 The ACRITAMER 505E carbomer was substituted CARBOPOL® ULTREZ 10 polymer. It was noted that when the ULTREZ® 10 carbomer was added at a level of 0.5–0.6% in addition to Dow Corning® Wax 580 (0.2–1.0%) the formulation provided a stable and compatible lotion-like gel with cosmetic appearance. The viscosity of ULTREZ®-10 containing base formulations found to be 21,600 cps, when recorded on Brookfield viscometer using spindle #4. Upon addition of benzethonium chloride 0.2% and disodium EDTA 0.05 to the carbomer base, a reduction in the viscosity of base formulations was noted.

| Formulation | Viscosity (cps) | Viscosity Reduction (%) |
|---|---|---|
| Base Formulation with ULTREZ ® 10 | 21,600 | — |
| Base formulation with ULTREZ ® 10 and benzethonium chloride | 7,200 | 66.67 |
| Base formulation with ULTREZ ® 10 and disodium EDTA | 12,540 | 41.94 |

In general, carbomers are susceptible or vulnerable to charged molecules like chlorhexidine gluconate, benzalkonium chloride, benzethonium chloride as well as salts like disodium EDTA. The sensitivity of the carbomers is exemplified to a moderate degree with ACRITAMER 505E. In the present invention, ULTREZ® 10, the most preferred carbomer, exhibited tolerance to the addition of ionic or charged molecules with formulating and cosmetic advantages.

EXAMPLE 3

Formulation 9 Formulation 5 was used again as a standard and lemon grass oil 2% and Autralian tea tree oil 2% were added to the formulation. The viscosity of the formulation was 14,000.

Formulation 10 To Formulation 9, PHOSPHOLIPID CDM 0.05 and tocopheryl acetate 0.025 was added. The viscosity of the formulation was 10,350.

Formulation 11 To Formulation 10, benzethonium chloride 0.2 was added. The viscosity of the resulting formulation decreased to 6,420.

Formulation 12 Instead of the 70% ethyl alcohol used in Formulation 11, the 70% was made up of ethyl alcohol/iso-propyl alcohol/n-propyl alcohol in a 40:25:5 ratio. The viscosity of the resulting formulation was 8,820.

EXAMPLE 4

Formulation 13 A formulation was prepared with the following components: ethyl alcohol 62; ULTREZ® 10 0.55; glycerin 0.5; cyclomethicone (245) 1.25; dimethicone (225) 1.0; Dow Corning® 580 wax 0.025; SILSOFT® PEDM 0.2; CERAPHYL-41 1.0; CERAPHYL-28 0.5; phenoxyethanol 0.5, benzalkonium chloride (50% active) 0.2, PHOSPHOLIPID CDM 0.05; GERMABEN-II 0.1; AMP-95. The viscosity of the formulation was 17,300.

Formulation 14 Formulation 13 was used as a standard formulation using ethyl alcohol 70, ULTREZ®-10 0.6, glycerin 1.5, cyclomethicone (245) 0.5, dimethicone (245) 1.0,Dow Corning® 580 wax 0.25, SILSOFT® PEDM 1.0, CERAPHYL-28 0.5, CERAPHYL-41 0.5. The phenoxyethanol 0.5, benzalkonium chloride (50% active) 0.2, PHOSPHOLIPID CDM 0.05; GERMAL PLUS 0.1 was replaced with chlorhexidine gluconate (20% solution) at 0.5%. The resulting solution turned watery, with a viscosity of less than about 100.

Formulation 15 Formulation 14 was used and the chlorhexidine gluconate was replaced with about 0.1 COSMOCIL®. The resulting solution had a viscosity of less than about 100.

Compositions containing ULTREZ® 10 with charged molecules like benzethonium chloride and benzalkonium chloride at different concentrations did not demonstrate any significant stability or viscosity effects. Other antimicrobial compounds such as guanides, including chlorhexidine gluconate and polyhexamethylene biguanide (PHMB, COSMOCIL®) at different concentrations destabilized the compositions, resulting in the undesirably low viscosities.

EXAMPLE 5

Compositions of the present invention were tested for irritation and sensitivity. The following formulations were prepared:

Formulation 16 deionized water 28.7, ethyl alcohol 62, ULTREZ® 10 0.45, glycerin 0.5, cyclomethicone 1.25, Dow Corning® 580 Wax 0.025, SILSOFT® PEDM 0.2, CERAPHYL®-28 0.5, CERAPHYL®-41 1.0, AMP 95 (pH adjuster) as needed, 1906 AD MOD I 0.1.

Formulation 17 deionized water 27.7, ethyl alcohol 62, ULTREZ® 10 0.55, glycerin 0.5, cyclomethicone 1.25, Dow Corning 580 Wax 0.025, SILSOFT® PEDM 0.2, CERAPHYL®-28 0.5, CERAPHYL®-41 1.0, AMP 95 (pH adjuster) as needed, 1906 AD MOD I 0.06, phenoxy ethanol 0.5, benzalkonium chloride (50% active) 0.16, benzethonium chloride 0.08, PHOSPHOLIPID CDM 0.05, GERMALL Plus 0.1, GERMABEN II 0.1.

Prior to study the subjects were screened to assure that they met the inclusion/exclusion criteria. Each subject was provided with a schedule of the study activities. The Induction Phase consisted of nine (9) consecutive applications of the study material and subsequent evaluations of the study sites were assessed. prior to the applications of the patches, the sites were outlined with a skin marker, e.g., gentian violet. The subjects were required to remove the patches approximately 24 hours after application. The subjects returned to the facility at 48 hour intervals to have the sites evaluated and identical patches reapplied. Following the ninth evaluation, the subjects were dismissed for a 10–14 day rest period. After the rest period, the challenge period was initiated during the 6th week of the study with the identical patches applied to the sites previously unexposed to the study. These patches were removed by subjects after 24 hours and the sites graded after additional 24-hour and 48 hour periods. The gradings were done 48 and 72 hours after application. To be considered a completed case, a subject must have nine (9) applications and no less than eight (8) subsequent readings during induction and one (1) product application and two (2) readings during the challenge. Of the 101 subjects that completed the study, there was no evidence of sensitization or irritation to the formulations.

EXAMPLE 6

The two formulations employed in Example 5 above were investigated to determine their moisturizing capabilities. Fifteen subjects applied the formulations to the dry skin on the lateral aspect of the lower leg. The moisturization of the skin was measured using the SKICON® Skin Surface Hydrometer. The results indicated that Formulation 17 behaved similarly to the untreated control indicating that the formulation was non-drying. Formulation 16 was found to be similar to Formulation 17 but slightly more drying. Both formulations were surprising in that for formulations containing high levels of alcohol the products were not found to possess significant drying effects.

We claim:

1. An antimicrobial composition comprising:
at least about 40 percent by weight alcohol, a thickener consisting of an effective amount of a carbomer polymer, wherein the carbomer polymer is a modified acrylic copolymer comprising of a major portion of a monoolefinically unsaturated carboxylic acid monomer or its anhydride having a length of from about 3 to 6 carbon atoms and a minor portion of a $C_8$–$C_{30}$ chain acrylate or methacrylate ester monomer wherein the carboxylic acid or its anhydride is from about 80 to about 99% by weight and the a $C_8$–$C_{30}$ chain acrylate or methacrylate ester monomer is from about 1 to about 20% by weight, an effective amount of a cationic antimicrobial compound, and water; the composition having a viscosity of greater than about 5,000 centipoise.

2. The antimicrobial composition of claim 1 wherein the alcohol is selected from the group consisting of ethyl alcohol, iso-propyl alcohol and n-propyl alcohol.

3. The antimicrobial composition of claim 1 wherein the cationic antimicrobial compound is selected from the group consisting of benzalkonium chloride, methyl benzethonium chloride and cetyl pyridinium chloride.

4. The antimicrobial composition of claim 1 which additionally comprises phenylethyl dimethicone from about 0.1 to about 2.0 weight percent and stearoxytrimethylsilane from about 0.1 to about 1.0 weight percent.

5. The antimicrobial composition of claim 1 which additionally comprises cetyl lactate from about 0.3 to about 1.5 weight percent and $C_{12}$–$C_{15}$ alkyl lactates from about 0.2 to about 2.0 weight percent.

6. The antimicrobial composition of claim 4 wherein the antimicrobial composition additionally contains cyclomethicone from about 0.75 to about 5.0 weight percent.

7. The composition of claim 1 wherein the carbomer polymer is present from about 0.2 to about 2.0 percent by weight.

8. The composition of claim 1 wherein the carbomer polymer is present from about 0.05 to about 0.5 percent by weight.

9. The composition of claim 1 which additionally contains an effective amount of an emollient.

10. The composition of claim 1 which additionally contains an effective amount of a moisturizer.

11. A method for disinfecting a surface comprising applying to the surface an effective amount of the antimicrobial composition of claim 1.

12. The method of claim 11 wherein the surface is hands, wound site, infected site, presurgical cutaneous site, acne site, injection site or a hard surface.

13. The method of claim 11 wherein the surface is skin.

14. An antimicrobial composition consisting essentially of:
at least about 40 percent by weight alcohol, a thickener consisting of an effective amount of a carbomer polymer, wherein the carbomer polymer is a modified acrylic copolymer comprising of a major portion of a monoolefinically unsaturated carboxylic acid monomer or its anhydride having a length of from about 3 to 6 carbon atoms and a minor portion of a $C_8$–$C_{30}$ chain acrylate or methacrylate ester monomer wherein the carboxylic acid or its anhydride is from about 80 to about 99% by weight and the a $C_8$–$C_{30}$ chain acrylate or methacrylate ester monomer is from about 1 to about 20% by weight, an effective amount of a cationic antimicrobial compound, and water; the composition having a viscosity of greater than about 5,000 centipoise.

15. The antimicrobial composition of claim 1 wherein the viscosity is from about 9,000 to about 22,000 centipoise at 25° C.

16. The antimicrobial composition of claim 1 wherein the viscosity is from about 11,000 to about 20,000 centipoise at 25° C.

* * * * *